(12) United States Patent
Mukai

(10) Patent No.: US 10,182,928 B2
(45) Date of Patent: Jan. 22, 2019

(54) MEDICAL TUBULAR BODY

(71) Applicant: KANEKA CORPORATION, Osaka-shi, Osaka (JP)

(72) Inventor: Yuki Mukai, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 133 days.

(21) Appl. No.: 14/782,133

(22) PCT Filed: Feb. 25, 2014

(86) PCT No.: PCT/JP2014/054563
§ 371 (c)(1),
(2) Date: Oct. 2, 2015

(87) PCT Pub. No.: WO2014/171184
PCT Pub. Date: Oct. 23, 2014

(65) Prior Publication Data
US 2016/0058590 A1    Mar. 3, 2016

(30) Foreign Application Priority Data

Apr. 16, 2013  (JP) .................................. 2013-086133

(51) Int. Cl.
*A61F 2/915*    (2013.01)
*A61F 2/844*    (2013.01)
(Continued)

(52) U.S. Cl.
CPC .............. *A61F 2/915* (2013.01); *A61F 2/844* (2013.01); *A61F 2/88* (2013.01); *A61F 2/962* (2013.01);
(Continued)

(58) Field of Classification Search
CPC ......................... A61F 2/915; A61F 2250/0098
See application file for complete search history.

(56) References Cited

U.S. PATENT DOCUMENTS 6,273,913 B1   8/2001  Wright et al.
8,029,561 B1  10/2011  Kopia et al.
(Continued)

FOREIGN PATENT DOCUMENTS

JP    2002-272855 A   9/2002
JP    2003-527925 A   9/2003
(Continued)

OTHER PUBLICATIONS

International Search Report, issued in PCT/JP2014/054563, dated Apr. 22, 2014.

*Primary Examiner* — Diane Yabut
(74) *Attorney, Agent, or Firm* — Birch, Stewart, Kolash & Birch, LLP

(57) ABSTRACT

An object of the present invention is to provide a medical tubular body that is excellent in visibility under X-ray fluoroscopic control, insertion property into a catheter and sliding property in a catheter, that suppresses contact of a marker with a tubular body or an adjacent marker in a diameter reduction state, and that is able to further reduce its diameter. The present invention provides a medical tubular body 100 comprising a tubular body whose diameter is expandable and a marker 121 provided inside the tubular body.

16 Claims, 13 Drawing Sheets

(51) Int. Cl.
  *A61F 2/88* (2006.01)
  *A61F 2/962* (2013.01)
  *A61F 2/82* (2013.01)

(52) U.S. Cl.
  CPC .................. *A61F 2002/825* (2013.01); *A61F 2002/91558* (2013.01); *A61F 2230/0082* (2013.01); *A61F 2250/0063* (2013.01); *A61F 2250/0098* (2013.01)

(56) References Cited

U.S. PATENT DOCUMENTS

| | | |
|---|---|---|
| 2001/0027340 A1 | 10/2001 | Wright et al. |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0016625 A1 | 2/2002 | Falotico et al. |
| 2002/0051730 A1 | 5/2002 | Bodnar et al. |
| 2002/0094440 A1 | 7/2002 | Llanos et al. |
| 2002/0111590 A1 | 8/2002 | Davila et al. |
| 2002/0133183 A1 | 9/2002 | Lentz et al. |
| 2002/0143386 A1 | 10/2002 | Davila et al. |
| 2002/0165608 A1 | 11/2002 | Llanos et al. |
| 2002/0190858 A1 | 12/2002 | Holmes et al. |
| 2002/0193867 A1 | 12/2002 | Gladdish, Jr. et al. |
| 2003/0023299 A1 | 1/2003 | Amplatz et al. |
| 2003/0060877 A1 | 3/2003 | Falotico et al. |
| 2003/0065345 A1 | 4/2003 | Weadock |
| 2003/0065346 A1 | 4/2003 | Evens et al. |
| 2003/0065377 A1 | 4/2003 | Davila et al. |
| 2003/0176915 A1 | 9/2003 | Wright et al. |
| 2003/0204168 A1 | 10/2003 | Bosma et al. |
| 2003/0216699 A1 | 11/2003 | Falotico |
| 2004/0102758 A1 | 5/2004 | Davila et al. |
| 2004/0197372 A1 | 10/2004 | Llanos et al. |
| 2004/0243097 A1 | 12/2004 | Falotico et al. |
| 2004/0254627 A1 | 12/2004 | Thompson et al. |
| 2004/0260268 A1 | 12/2004 | Falotico et al. |
| 2005/0002986 A1 | 1/2005 | Falotico et al. |
| 2005/0004663 A1 | 1/2005 | Llanos et al. |
| 2005/0033261 A1 | 2/2005 | Falotico et al. |
| 2005/0085902 A1 | 4/2005 | Wright et al. |
| 2006/0060266 A1 | 3/2006 | Bales et al. |
| 2006/0064154 A1 | 3/2006 | Bales et al. |
| 2006/0064155 A1 | 3/2006 | Bales et al. |
| 2006/0064158 A1 | 3/2006 | Bales et al. |
| 2006/0222756 A1 | 10/2006 | Davila et al. |
| 2006/0235503 A1 | 10/2006 | Llanos et al. |
| 2006/0282160 A1 | 12/2006 | Wright et al. |
| 2007/0021825 A1 | 1/2007 | Wright et al. |
| 2007/0026036 A1 | 2/2007 | Falotico et al. |
| 2007/0087028 A1 | 4/2007 | Falotico et al. |
| 2007/0100436 A1 | 5/2007 | Wright et al. |
| 2007/0179594 A1 | 8/2007 | Llanos et al. |
| 2007/0179595 A1 | 8/2007 | Davila et al. |
| 2007/0179596 A1 | 8/2007 | Davila et al. |
| 2007/0179597 A1 | 8/2007 | Davila et al. |
| 2007/0276473 A1 | 11/2007 | Llanos et al. |
| 2007/0276474 A1 | 11/2007 | Llanos et al. |
| 2007/0276475 A1 | 11/2007 | Llanos et al. |
| 2007/0276476 A1 | 11/2007 | Llanos et al. |
| 2008/0051865 A1 | 2/2008 | Llanos et al. |
| 2008/0051883 A1 | 2/2008 | Llanos et al. |
| 2008/0051884 A1 | 2/2008 | Llanos et al. |
| 2008/0051885 A1 | 2/2008 | Llanos et al. |
| 2008/0317827 A1 | 12/2008 | Wright et al. |
| 2009/0204204 A1 | 8/2009 | Falotico et al. |
| 2009/0306760 A1* | 12/2009 | Hebert ............... A61F 2/91 623/1.12 |
| 2009/0306761 A1 | 12/2009 | Hebert et al. |
| 2010/0057192 A1 | 3/2010 | Celermajer |
| 2010/0239636 A1 | 9/2010 | Wright et al. |
| 2010/0249909 A1 | 9/2010 | McNamara et al. |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0268329 A1 | 10/2010 | Falotico et al. |
| 2010/0285089 A1 | 11/2010 | Llanos et al. |
| 2010/0298755 A1 | 11/2010 | McNamara et al. |
| 2011/0071623 A1 | 3/2011 | Finch et al. |
| 2011/0071624 A1 | 3/2011 | Finch et al. |
| 2011/0177152 A1 | 7/2011 | Falotico et al. |
| 2011/0257723 A1 | 10/2011 | McNamara |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2012/0029475 A1 | 2/2012 | Kopia et al. |
| 2012/0053686 A1 | 3/2012 | McNamara et al. |
| 2012/0130301 A1 | 5/2012 | McNamara et al. |
| 2012/0172976 A1 | 7/2012 | Wright et al. |
| 2012/0226347 A1 | 9/2012 | Falotico et al. |
| 2012/0253455 A1 | 10/2012 | Gladdish, Jr. et al. |
| 2012/0259263 A1 | 10/2012 | Celermajer et al. |
| 2012/0265296 A1 | 10/2012 | McNamara et al. |
| 2012/0289882 A1 | 11/2012 | McNamara et al. |
| 2012/0290062 A1 | 11/2012 | McNamara et al. |
| 2012/0330401 A1 | 12/2012 | Sugimoto et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0211492 A1 | 8/2013 | Schneider et al. |
| 2013/0231737 A1 | 9/2013 | McNamara et al. |
| 2013/0267885 A1 | 10/2013 | Celermajer et al. |
| 2014/0012368 A1 | 1/2014 | Sugimoto et al. |
| 2014/0134225 A1 | 5/2014 | Falotico et al. |
| 2014/0194971 A1 | 7/2014 | McNamara |
| 2014/0257167 A1 | 9/2014 | Celermajer |
| 2014/0303717 A1 | 10/2014 | Wright et al. |
| 2015/0127083 A1 | 5/2015 | Hebert et al. |
| 2015/0148731 A1 | 5/2015 | McNamara et al. |

FOREIGN PATENT DOCUMENTS

| | | |
|---|---|---|
| JP | 2003-334256 A | 11/2003 |
| JP | 2008-511423 A | 4/2008 |
| WO | WO 2011/093941 A2 | 8/2011 |
| WO | WO 2011/122444 A1 | 10/2011 |
| WO | WO 2012/031748 A2 | 3/2012 |

* cited by examiner (a)

(b)

(a)

(b)

(a)

(b)

(a)

(b)

(a)

(b)

(a)

(b)

(a)

(b)

MEDICAL TUBULAR BODY

TECHNICAL FIELD

The present invention relates to a medical tubular body whose diameter is expandable, that is used to treat a stenotic or occluded lesion of blood vessels and other biological lumen, for example. In more detail, the present invention relates to a medical tubular body represented by a stent, that is placed in a lesion of a biological lumen, or a medical tubular body that is used to remove a thrombus or others occurred in a lesion.

BACKGROUND ART

A medical tubular body represented by a stent is a medical instrument for treating various diseases caused by stenosis or occlusion of blood vessels and other biological lumens, generally. Examples of the medical tubular body include that which expands a lesion, such as stenosis or occlusion site, from inside and then is placed in the lesion to maintain the inner diameter of the lumen, and that which tangles in a thrombus or others occurred in a lesion or around it to eliminate from the body, thereby restoring the inner diameter of the lumen in the lesion.

The medical tubular body is used in a body, and once the medical tubular body is put into a body, it is impossible to confirm its position visually. Therefore, a marker containing an X-ray opaque material is mounted to a predetermined position of the medical tubular body, and an operation is conducted while checking the exact position of this marker under X-ray fluoroscopic control.

It is required to improve visibility of the marker in terms of accurate conveyance (delivery) to a lesion and position adjustment of an accurate expansion range (i.e., a working range) in an expanded state.

For example, FIG. 14 of Patent Literature 1 discloses an intraluminal medical device (a medical tubular body) that is able to be inserted into a delivery system having a small diameter by making its maker long in an axial direction and short in a radial direction.

Further, Patent Literature 2 describes a medical tubular body in which markers are provided at a circumference of an end part of the tubular body and arranged so as to be spaced from each other at a predetermined distance in order to facilitate determination of the direction of the medical tubular body.

CITATION LIST

Patent Literature

Patent Literature 1
  Japanese Unexamined Laid-open Patent Application Publication No. 2003-334256
Patent Literature 2
  Japanese Unexamined Laid-open Patent Application Publication No. 2003-527925

SUMMARY OF INVENTION

Technical Problem

However, in the medical tubular body disclosed in Patent Literatures 1 and 2, there is a limit for further improving visibility of the marker and performances such as insertion property into a catheter or sliding property in a catheter, depending on the feature of each configuration. Enlarging the marker simply or increasing the number of the marker, in order to improving the visibility of the marker, results in inhibiting the tubular body from inserting into a catheter or sliding in it. This is because the marker contact with a strut, which constitutes a part of the tubular body, or an adjacent marker in reducing the tubular body in diameter, resulting in unable to make the outer diameter of the tubular body small enough in the diameter reduction state.

An object of the present invention is to provide a medical tubular body that is excellent in visibility under X-ray fluoroscopic control, insertion property into a catheter and sliding property in a catheter, that suppresses contact of a marker with a tubular body or an adjacent marker in a diameter reduction state, and that is able to further reduce its diameter.

Solution to Problem

The present inventors conducted detailed studies for various shapes and others of the marker in order to solve the above problems. The present inventors considered in our study to utilize a remaining space inside the tubular body when the medical tubular body is reduced in diameter and completed the present invention by placing the marker at this inner space.

That is, a medical tubular body of the present invention which is able to solve the above problem comprises a tubular body whose diameter is expandable and a marker provided inside the tubular body. In the medical tubular body of the present invention, since the marker is provided inside the tubular body whose diameter is expandable, an inner space of the tubular body is utilized effectively and the marker is able to be placed in the space when the tubular body is reduced in diameter. Therefore, the markers do not contact with each other or the marker does not contact with the tubular body, or the degree of the contact is more reduced than ever before even if the contact occurs. As a result, the diameter of the tubular body in the reduced state can be made smaller than ever before.

In the medical tubular body, it is the preferred embodiment that the marker is fixed to an inner surface of the tubular body. This is because if the marker is provided also at other than the inner surface of the tubular body, such as, for example, an outer surface of the tubular body, the outer shape of the medical tubular body can not be made small enough.

In the medical tubular body, the marker is preferably provided at a non-deformation part which constitutes a part of the tubular body. In the case where the marker is provided at a part of the tubular body that deforms along with increase or decrease of the diameter of the tubular body, there is a risk that the marker comes off from the tubular body with the deformation of the tubular body. On the other hand, when the marker is provided at a part which does not deform along with increase or decrease of the diameter (namely the non-deformation part), the medical tubular body in which the risk of loss of the marker is reduced can be provided.

In the medical tubular body, the marker is preferably provided at a planer part of the inner surface of the tubular body. When the inner surface of the tubular body is made plane, a contact area of the marker with the inner surface of the tubular body is easily increased, and therefore, the marker can be fixed to the tubular body more firmly.

In the medical tubular body, the marker is preferably welded to the inner surface of the tubular body. Thereby, the medical tubular body in which the risk of loss of the marker is reduced can be provided.

In the medical tubular body, the marker has a size so as to be placed in the inner space of the tubular body in a state where the tubular body is reduced in diameter. When the marker has a size so as to be placed in the inner space of the tubular body in the state where the tubular body is reduced in diameter, the marker does not contact with the tubular body, and therefore, the outer shape of the medical tubular body can be made small enough.

It is preferred that the medial tubular body comprises at least two of the markers, wherein the markers have a size so as not to contact with each other in the state where the tubular body is reduced in diameter. When the markers do contact with each other, the outer shape of the medical tubular body can be made small enough.

In the medical tubular body, it is preferred that the two of the markers are provided at different positions in an axial direction of the tubular body. Even when the tubular body has a configuration so that the single marker can be placed inside it, in the case where the two markers exist in the same space inside the tubular body, the markers may contact with each other depending on their sizes. Therefore, when the two of the markers are provided at different positions in the axial direction of the tubular body, the contact of the markers with each other can be prevented, thereby making the outer shape of the medical tubular body small enough.

It is preferred that the medical tubular body further comprises a plurality of support rods whose lengths are different from each other, wherein the marker is provided at an end part of each of the support rod. When the support rods whose lengths are different from each other are used, it becomes easy to provide the markers at different positions in the axial direction of the tubular body.

It is the preferred embodiment that clearance is formed between one end of the marker and the tubular body in the state where the tubular body is reduced in diameter. The tubular body does not necessarily work such that the diameter of the tubular body reduces as designed, and therefore, remaining some extent of the space may have an advantage in the reduction of the diameter.

In the medical tubular body, the embodiment that the marker is longer in the axial direction of the tubular body than in a radial direction of the tubular body may be employed. In the medical tubular body of the present invention, the inner space of the tubular body is utilized for disposing the marker thereat; however, there is a limit to capacity of the inner space of the tubular body, of course, and so the volume of the marker is able to be increased by forming the marker longer in the axial direction.

It is preferred that the medial tubular body is self-expandable. Since the medical tubular body of the present invention is formed that the marker projects toward the inside of the tubular body, the medical tubular body of a self-expandable type is preferably employed rather than that of a balloon type.

In the medical tubular body, it is preferred that the tubular body has a net-like structure configured by a combination of a sequence of cells aligned in a helical direction.

In the medical tubular body, it is preferred that the marker has a columnar shape.

Advantageous Effects of Invention

Since the medical tubular body of the present invention comprises a tubular body whose diameter is expandable and a marker provided inside the tubular body, the markers do not contact with each other or the marker does not contact with the tubular body, or the degree of the contact is more reduced than ever before even if the contact occurs. As a result, the diameter of the tubular body in the reduced state can be made smaller than ever before.

DESCRIPTION OF THE PREFERRED EMBODIMENTS

Figure 1:
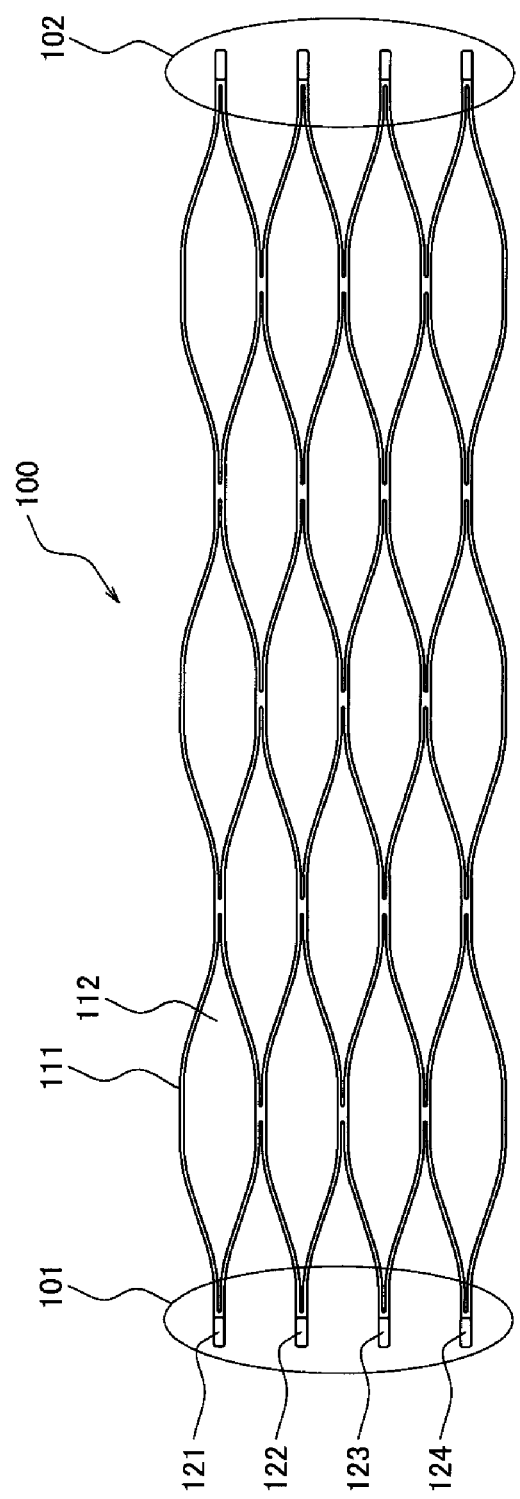
FIG. 1 shows a developed view of a medical tubular body according to a first embodiment of the present invention.

A medical tubular body of the present invention comprises a tubular body whose diameter is expandable and a marker provided inside the tubular body. In the medical tubular body of the present invention, since the marker is provided inside the tubular body whose diameter is expandable (i.e., an inner side of the tubular body in a radial direction), the marker is able to be placed in an inner space of the tubular body when the tubular body is reduced in diameter. Therefore, the markers do not contact with each other or the marker does not contact with the tubular body, or the degree of the contact is more reduced than ever before even if the contact occurs. In the present specification, a structure excluding the marker from the medical tubular body is referred to as a "tubular body".

(1) Application of the Medical Tubular Body

The medical tubular body is used in a biological lumen, and examples of the medical tubular body include, for example, a stent that is placed in a lesion of a biological lumen to maintain or expand the diameter of the biological lumen, a thrombus recovery device that removes a thrombus formed in a biological lumen, and a peripheral protection device such as a peripheral protection filter.

(2) Classification of the Medical Tubular Body

There are some types in the medical tubular body, such as, for example, (i) a coiled type formed from one line-shaped metal or polymer material, (ii) a type made by cutting out from a metal tube with laser or the like, (iii) a type made by welding linear parts and assembling them, and (iv) a type made by weaving a plurality of metal wires.

The medical tubular body is used to be attached to a catheter (a delivery system: a carrier device) or the like, that has a part for installing the medical tubular body to convey to a lesion (delivery). In terms of expansion mechanisms, the medical tubular body can be classified into (i) a balloon expanding type that is loaded (mounted) on an outer surface of a balloon to be conveyed to a lesion and is expanded by the balloon at the lesion and (ii) a self-expandable type that is conveyed to a lesion by a catheter equipped with an expansion-suppressing member and expands by itself at the lesion by removing the expansion-suppressing member.

In the state where the medical tubular body is installed in the delivery system such as a balloon and a catheter, the medical tubular body decreases in size in a perpendicular direction to a longitudinal axis of the tubular body (i.e., the radial direction of the tubular body) and extends in the longitudinal axis direction, thereby changing in the diameter reduction state, a cylindrical form that is longer and thinner than in the expanded state. In the self-expandable type, since there is no need to provide a balloon inside it, the diameter in its reduced state is able to be made smaller than in the balloon expanding type.

(3) Tubular Body

The tubular body is a structure whose diameter is expandable, that has a net-like structure such as a mesh, for example. In the present invention, that the diameter is expandable means to be able to expand in the perpendicular direction to the longitudinal axis of the tubular body (i.e., the radial direction) and also be able to contract (reduce in diameter) in reverse from the state where the diameter is expanded. The tubular body is configured by a pattern of a sequence of structural elements connecting to each other, that expands and contracts in a circumferential direction and the axis direction, for example. In the present invention, the tubular body is applicable to any pattern, and therefore, the tubular body is not limited to a specific shape of any stent or a pattern of the structural elements.

(4) Marker

Once the medical tubular body is put into a body, it is impossible to confirm its position visually. Therefore, a marker containing an X-ray opaque material is mounted to a predetermined position of the medical tubular body so that the medical tubular body can be observed under X-ray fluoroscopic control. The marker does not necessarily completely cut off an X-ray and may have a certain degree of an X-ray transmission rate so that the existence of the marker under X-ray fluoroscopic control can be detected.

This application claims priority to Japanese Patent Application No. 2013-86133, filed on Apr. 16, 2013, the entire contents of which are incorporated by reference herein.

(Embodiment 1)

Figure 9:
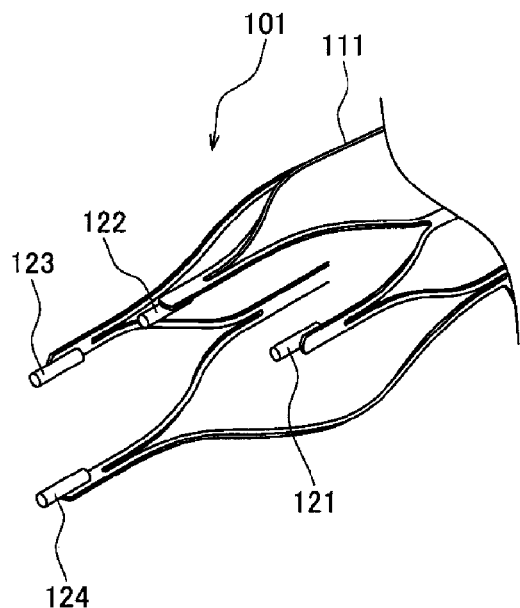
FIG. 9(a) shows a perspective view of an end part of the medical tubular body (in the diameter enlargement state) according to the fourth embodiment.
FIG. 9(b) shows a view of the medical tubular body (in the diameter enlargement state) according to the fourth embodiment seen from the axial direction.
Figure 9:
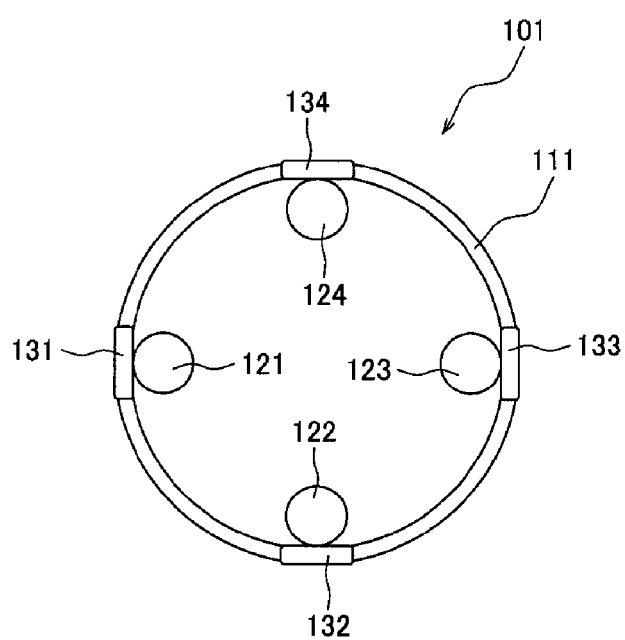
Figure 12:
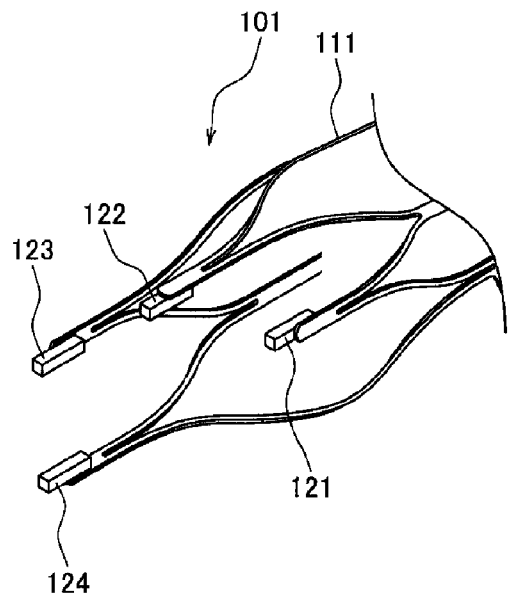
FIG. 12(a) shows a perspective view of an end part of the medical tubular body (in the diameter enlargement state) according to the fifth embodiment.
FIG. 12(b) shows a view of the medical tubular body (in the diameter enlargement state) according to the fifth embodiment seen from the axial direction.
Figure 12:
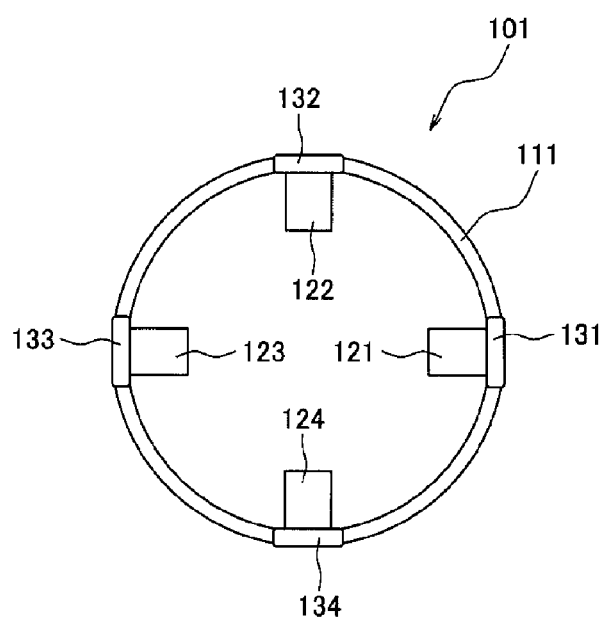

Hereinafter, a medical tubular body according to a first embodiment of the present invention is explained, referring to the drawings. FIG. 1 shows a developed view of a medical tubular body according to the first embodiment of the present invention. A medical tubular body 100 has a distal end 101 and a proximal end 102, and comprises a metal mesh 111 provided between the distal end 101 and the proximal end 102. The metal mesh 111 is configured by a combination of a sequence of cells 112. The metal mesh 111 is rolled around a center axis extending in a longitudinal direction and then two long sides of the metal mesh 111 are joined to each other, thereby forming a tubular body. With regard to this, FIG. 9(a) and FIG. 12(a) are of some help.

The medical tubular body 100 according to the first embodiment of the present invention comprises a marker housing at, for example, the distal end 101 or the proximal end 102 and markers 121 to 124 fixed to the marker housings. The marker housing is explained below, referring to an enlarged view around the marker 121 of the medical tubular body 100.

Figure 2:
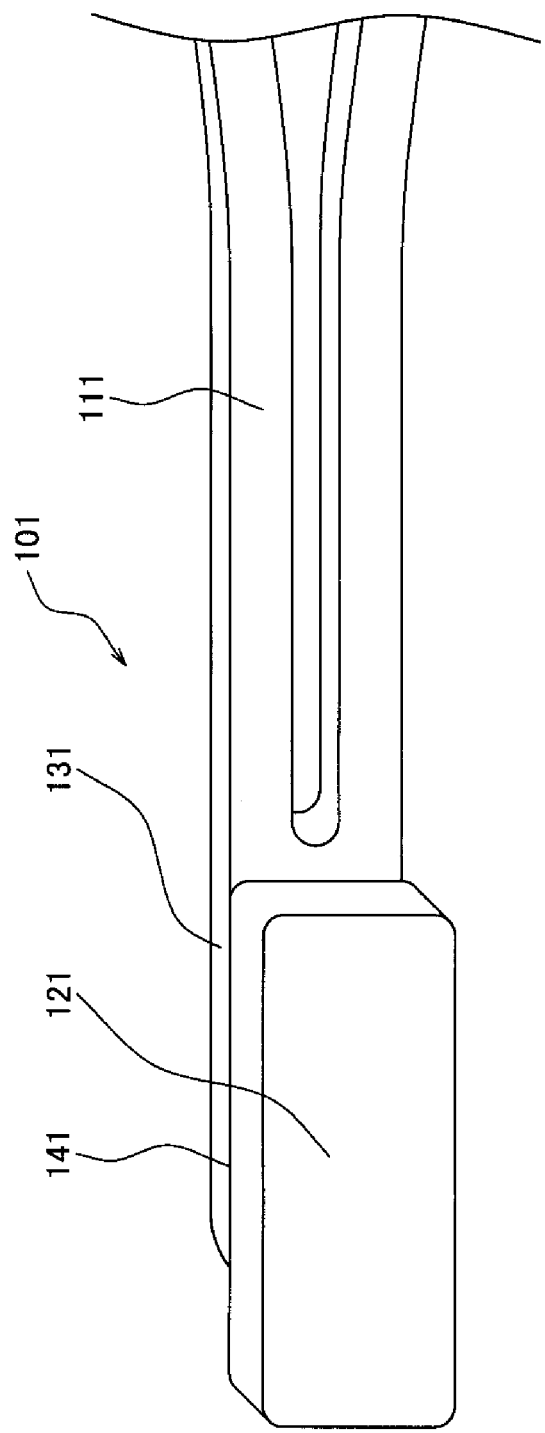
FIG. 2 shows an enlarged view of an end part of the medical tubular body according to the first embodiment of the present invention.

FIG. 2 shows an enlarged view around the marker 121 of the medical tubular body 100 according to the first embodiment of the present invention. In FIG. 2, the marker 121 is fixed to an inner surface of the marker housing 131 (i.e., the inner surface of the tubular body) formed at the distal end 101.

A materials used for the metal mesh 111 is not particularly limited, as long as it is able to withstand a load of strength during transformation of the diameter expanding or reducing and in indwelling; and 316L stainless steel as a medical-use stainless steel, tantalum, Co—Cr (cobalt-chrome) alloys, Ni—Ti (nickel-titanium) alloys and the others can be preferably used. In particular, nickel-titanium alloys are preferably used, since they have a shape memory property and an elastic property and is excellent in workability. Among the nickel-titanium alloys, an alloy containing about 50 mass % to about 60 mass % of nickel is preferably used, particularly.

The metal mesh 111 may contain a biodegradable material such as biodegradable polymers or metals. Or, the biodegradable material may be a composite of at least two kinds of biodegradable polymers and/or metals.

As a manufacturing method of the metal mesh 111, a laser processing method, an electrical discharge machining method, a mechanical cutting processing method, an etching method or the like can be preferably adopted. In the present invention, a method of cutting a tubular material in a pattern of the cells 112 to form the tubular body, storing the shape in the state where the tubular body is expanded in diameter, and mounting the marker 121 and others to the inner side of the tubular body can be also preferably adopted.

It is preferable that the marker housing 131 is made of the same material as a material of the metal mesh 111, in terms of strength and corrosion resistance, and forms a unitary structure with the metal mesh 111.

The marker housing 131 has an inner surface, with respect to a radial direction, for mounting the marker 121. In the present invention, the marker housing 131 may have a shape and size so as to act as a base to which the marker 121 is mounted. Since the shape of the marker housing 131 is desired to be stable as the base for mounting the marker 121, the marker housing 131 is preferably a non-deformation (an immovable) part, that does not deform by expansion and contraction of the tubular body.

Figure 3:
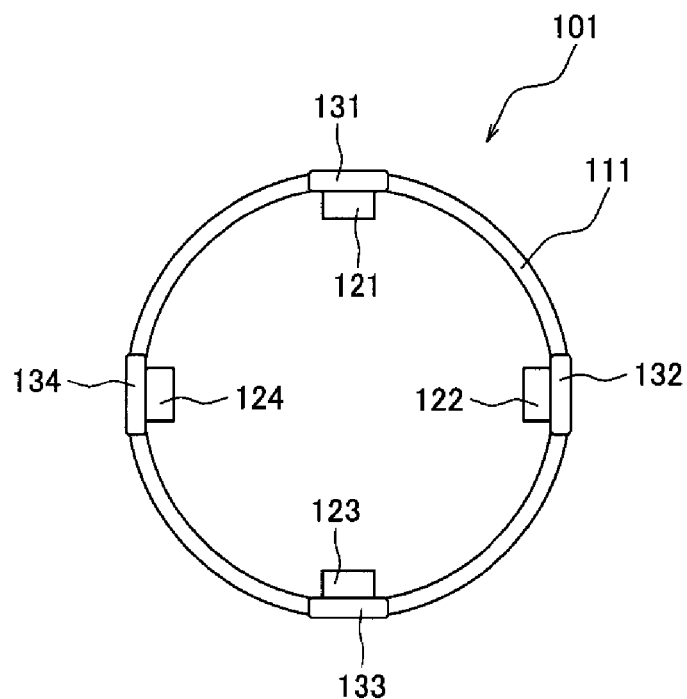
FIG. 3(a) shows a view of the medical tubular body (in the diameter enlargement state) according to the first embodiment seen from the axial direction.
FIG. 3(b) shows a view of the medical tubular body (in the diameter reduction state) according to the first embodiment seen from the axial direction.
Figure 3:
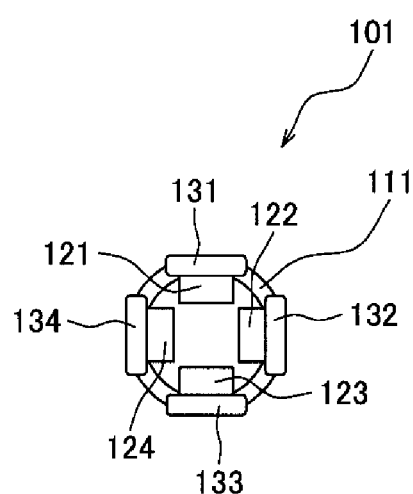

FIG. 3(a) shows a view of the distal end 101 of the medical tubular body (in the diameter enlargement state) 100 according to the first embodiment seen from the axial direction, and FIG. 3(b) shows a view of the distal end 101 of the medical tubular body (in the diameter reduction state) according to the first embodiment seen from the axial direction. As can be seen from FIGS. 3(a), (b), since the markers 121 to 124 are provided inside the tubular body which constitute the medical tubular body 100, an inner space of the tubular body is utilized effectively and the marker is able to be placed in the space even in the state where the medical tubular body 100 is reduced in diameter. Therefore, the markers do not contact with each other or the marker does not contact with the tubular body, or the degree of the contact is more reduced than ever before even if the contact occurs. As a result, the diameter of the tubular body in the reduced state can be made smaller than ever before.

It is preferred that the marker housings also do not contact with each other as well as the marker do not. Thus, it is preferred that the marker housings 131 to 134 have a size so as not to inhibit the medical tubular body 100 reducing in diameter, as they do not contact with each other in the state where the medical tubular body 100 is reduced in diameter. A sectional shape, in the direction perpendicular to the longitudinal axis of the medical tubular body 100, of the marker housings 131 to 134 can be, for example, a circle, an oval, an ellipse, a square, a rectangle, a rhombus.

A material which constitutes the marker 121 is not particularly limited, as long as it has a high X-ray opacity than the constituent material of the medical tubular body 100. In terms of effects on a living body or workability such as hardly-deformation in mounting to the marker housing 131, metal materials are preferable. Especially, platinum, palladium and tantalum are preferably used, since they are excellent in having good biological compatibility to a human body. In particular, in the case where the nickel-titanium alloy is used for the material of the marker housing, tantalum is preferably used since the difference in electrochemical potential comes to be small and corrosion is inhibited.

A method of mounting the markers 121 to 124 to the marker housing 131 to 134, respectively, is not particular limited, as long as the markers do not fall off during delivery of the medical tubular body 100 and the operation of the placement in the lesion. Examples of the method include, for example, welding, brazing, caulking and the like, and among them, the marker is preferably mounted by welding. This is because, in welding, a different material from the marker housing or the marker (e.g., wax) is not used. Meanwhile, in the case of brazing, a different material from the marker housing or the marker is used, and in the case of caulking, smoothness on an outer surface, with respect to the radial direction, of the marker housing is hardly obtained. In installing the marker by welding, it is desired that the inner surface 141 of the marker housing shown in FIG. 2 is flat, and it preferably has an oval shape, a square shape or a rectangular shape since it needs to have a linear length corresponding to the diameter of the welded spot.

The diameter of the welded spot is preferably 80% or less of the length of a short side of the fixing surface of the marker, more preferably 70% or less of that, and even more preferably 60% or less of that, in terms of not causing adverse effects on an X-ray fluoroscopic image. Meanwhile, in terms of securing an anchorage strength of the marker, the diameter of the welded spot is preferably 20% or more of the length of the short side of the fixing surface of the marker, more preferably 30% or more of that, and even more preferably 40% or more of that. Specifically, the diameter of the welded spot is preferably about 40 μm to 100 μm, and more preferably about 50 μm to 90 μm.

The size of the tubular body is not particularly limited, and in the first embodiment, the outer diameter of the tubular body is, for example, about 0.36 mm to 0.46 mm in the diameter reduction state and about 4.0 mm to 4.5 mm in the diameter enlargement state. The length of the marker in the axis direction is, for example, 1.0 mm to 5.0 mm, and the length of the marker in the radial direction of the tubular body is, for example, about 0.20 mm to 0.35 mm.

(Embodiment 2)

Figure 4:
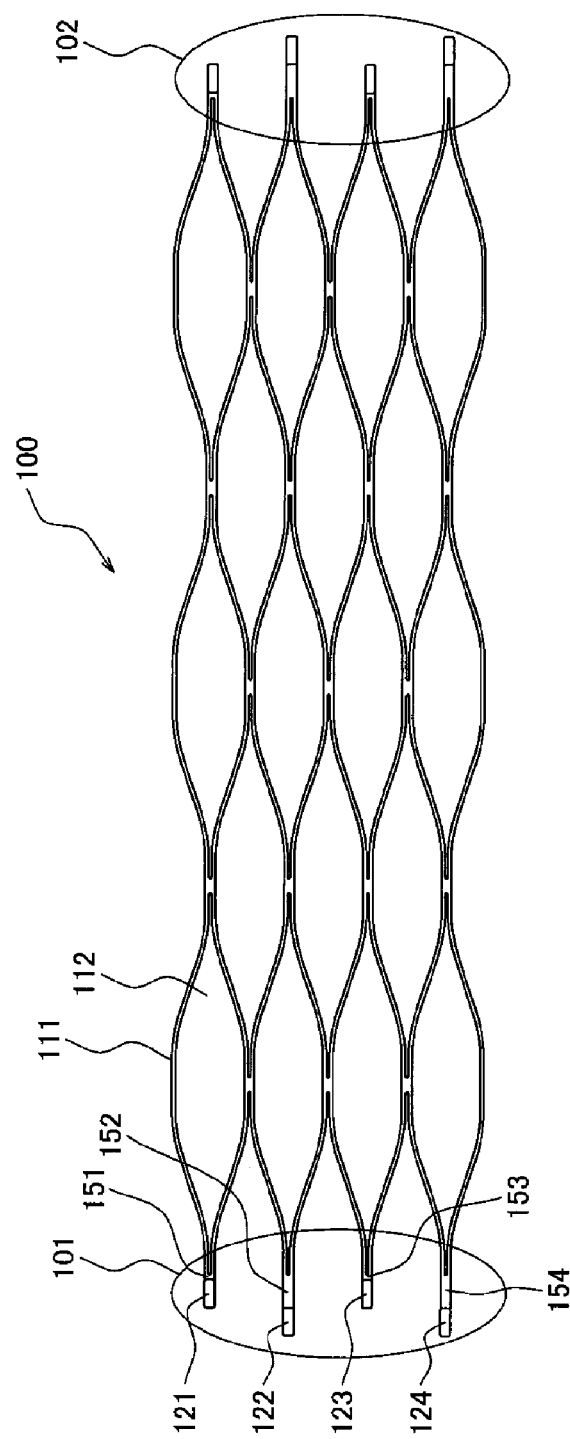
FIG. 4 shows a developed view of a medical tubular body according to a second embodiment of the present invention.

Hereinafter, a medical tubular body according to a second embodiment of the present invention is explained, referring to the drawings. FIG. 4 shows a developed view of a medical tubular body according to the second embodiment of the present invention. A medical tubular body 100 has a distal end 101 and a proximal end 102, and comprises a metal mesh 111 provided between the distal end 101 and the proximal end 102. The medical tubular body 100 according to the second embodiment of the present invention basically has the similar constitution to the medical tubular body 100 according to the first embodiment of the present invention, and therefore, the same element is assigned with the same reference numeral, thereby omitting the explanation of it.

The medical tubular body 100 according to the second embodiment of the present invention is different from the medical tubular body 100 according to the first embodiment in that: in the first embodiment, the markers 121 to 124 are disposed at same positions in the axial direction of the tubular body, whereas in the second embodiment, at least two of the markers, the marker 121 and the marker 122, are disposed at different positions in the axial direction of the tubular body. There are various specific embodiments for disposing the two markers at different positions in the axial direction of the tubular body, and as shown in FIG. 4, there is a method to make the lengths of a support rod 151 and a support rod 152 different from each other, wherein the support rod 151 connects the metal mesh 111 and the marker housing 131 (which is located behind the marker 121 and is not shown).

Figure 5:
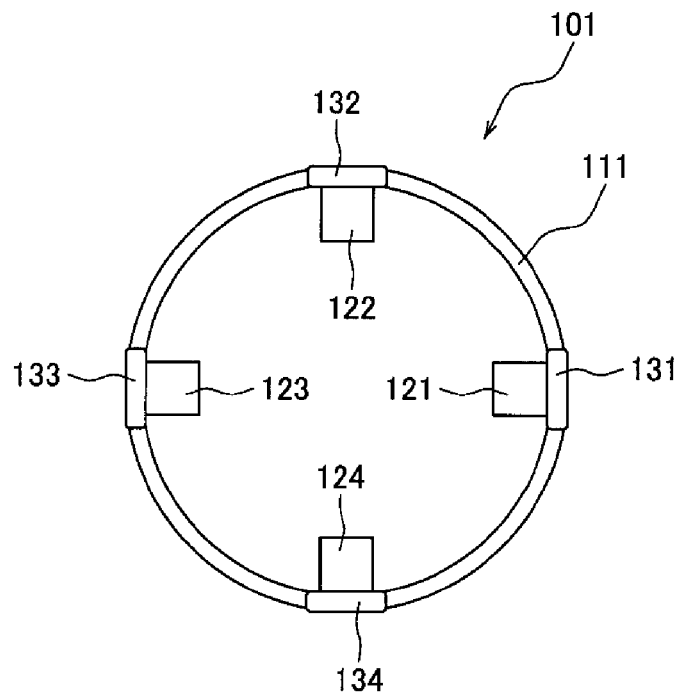
FIG. 5(a) shows a view of the medical tubular body (in the diameter enlargement state) according to the second embodiment seen from the axial direction.
FIG. 5(b) shows a view of the medical tubular body (in the diameter reduction state) according to the second embodiment seen from the axial direction.
Figure 5:
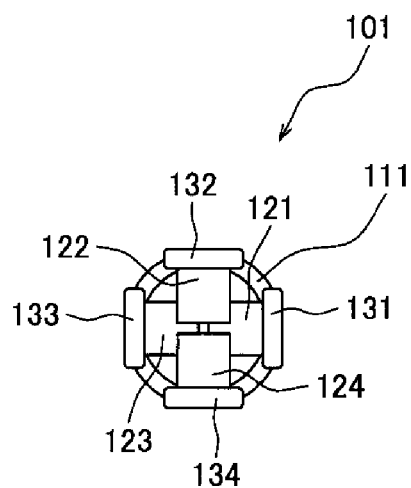

FIG. 5(a) shows a view of the distal end 101 of the medical tubular body (in the diameter enlargement state) 100 according to the second embodiment seen from the axial direction, and FIG. 5(b) shows a view of the distal end 101 of the medical tubular body (in the diameter reduction state) according to the second embodiment seen from the axial direction. As can be seen from FIGS. 5(a), (b), the same effect as the medical tubular body 100 according to the first embodiment is provided: since the markers 121, 122 are provided inside the tubular body, the inner space of the tubular body is utilized effectively and the marker is able to be placed in the space even in the state where the tubular body is reduced in diameter, and as a result, the diameter of the tubular body in the reduced state can be made smaller than ever before.

In addition to the above effect, as can be seen from FIG. 5(b), though the medical tubular body 100 comprises the two makers 121, 122, the marker 121 and the marker 122 are disposed at different positions in the axial direction of the tubular body, respectively, and so the marker 121 and the marker 122 can be placed in the inner space of the tubular body without interfering with each other in the state where the tubular body is reduced in diameter. In the case that the medical tubular body 100 comprises two or more of the markers like this, it can be seen that providing the respective markers at different positions in the axial direction of the tubular body is effective technique to decrease the diameter of the medical tubular body 100 in the reduced state.

A person skilled in the art could readily understand that the term "different positions in the axial direction of the tubular body" means "positions separated by at least length of the one marker in the axial direction of the tubular body so that the markers do not contact with each other".

(Embodiment 3)

Figure 6:
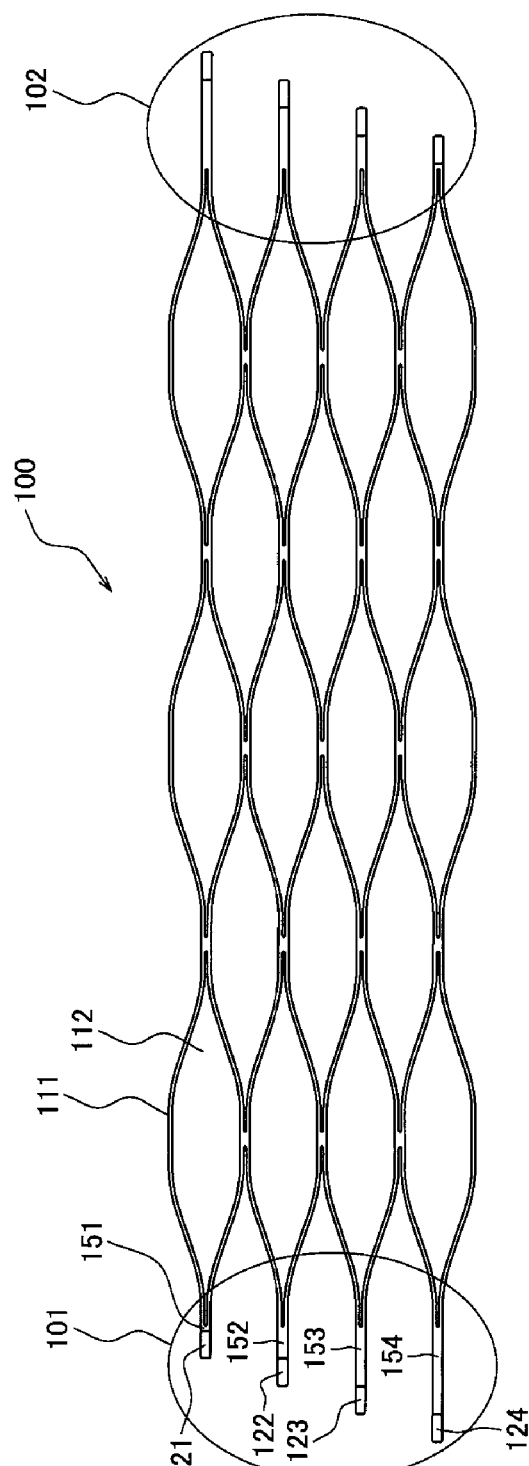
FIG. 6 shows a developed view of a medical tubular body according to a third embodiment of the present invention.

Hereinafter, a medical tubular body according to a third embodiment of the present invention is explained, referring to the drawings. FIG. 6 shows a developed view of a medical tubular body according to the third embodiment of the present invention. A medical tubular body 100 has a distal end 101 and a proximal end 102, and comprises a metal mesh 111 provided between the distal end 101 and the proximal end 102. The medical tubular body 100 according to the third embodiment of the present invention basically has the similar constitution to the medical tubular body 100 according to the second embodiment of the present invention, and therefore, the same element is assigned with the same reference numeral, thereby omitting the explanation of it.

The medical tubular body 100 according to the third embodiment of the present invention is different from the medical tubular body 100 according to the second embodiment in that: in the second embodiment, the lengths of the support rod 151 and the support rod 152 differ from each other, the lengths of the support rod 151 and the support rod 153 are same, and the lengths of the support rod 152 and the support rod 154 are also same, whereas in the third embodiment, the support rods 151 to 154 respectively have different length from each other.

Figure 7:
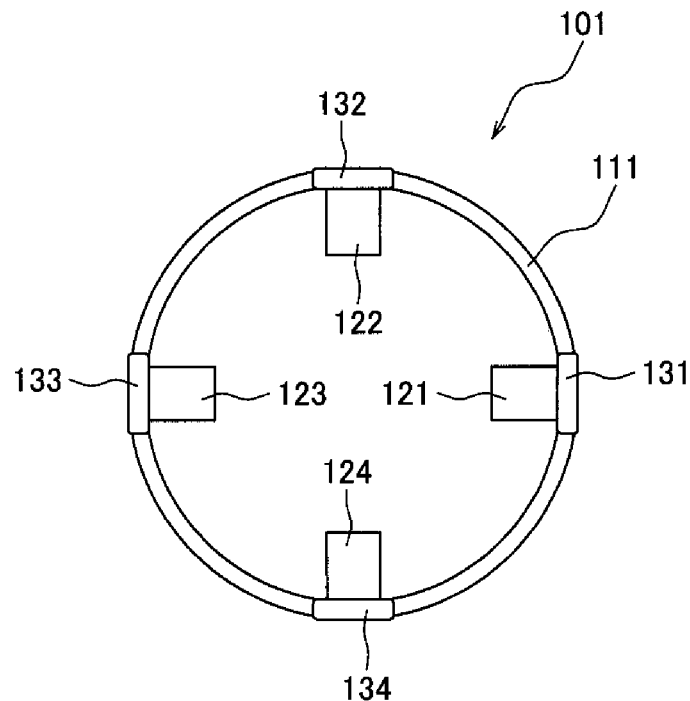
FIG. 7(a) shows a view of the medical tubular body (in the diameter enlargement state) according to the third embodiment seen from the axial direction.
FIG. 7(b) shows a view of the medical tubular body (in the diameter reduction state) according to the third embodiment seen from the axial direction.
Figure 7:
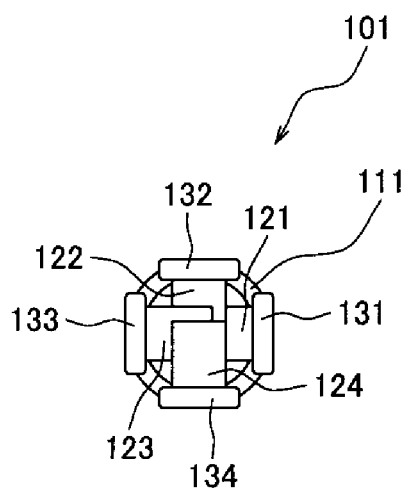

FIG. 7(a) shows a view of the distal end 101 of the medical tubular body (in the diameter enlargement state) 100 according to the third embodiment seen from the axial direction, and FIG. 7(b) shows a view of the distal end 101 of the medical tubular body (in the diameter reduction state) according to the third embodiment seen from the axial direction. As can be seen from FIG. 7(b), since the markers 121 to 124 are provided at different positions in the axial direction of the tubular body, the markers 121 to 124 can be placed in the inner space of the tubular body without interfering with each other when the tubular body is reduced in diameter. In the case that the medical tubular body 100 comprises two or more of the markers like this, it can be seen that providing the respective markers at different positions in the axial direction of the tubular body is effective technique to decrease the diameter of the medical tubular body 100 in the reduced state. This embodiment is advantageous in that positions of the markers 121 to 124 can be easily adjusted by changing the design of the lengths of the support rods.

(Embodiment 4)

Figure 8:
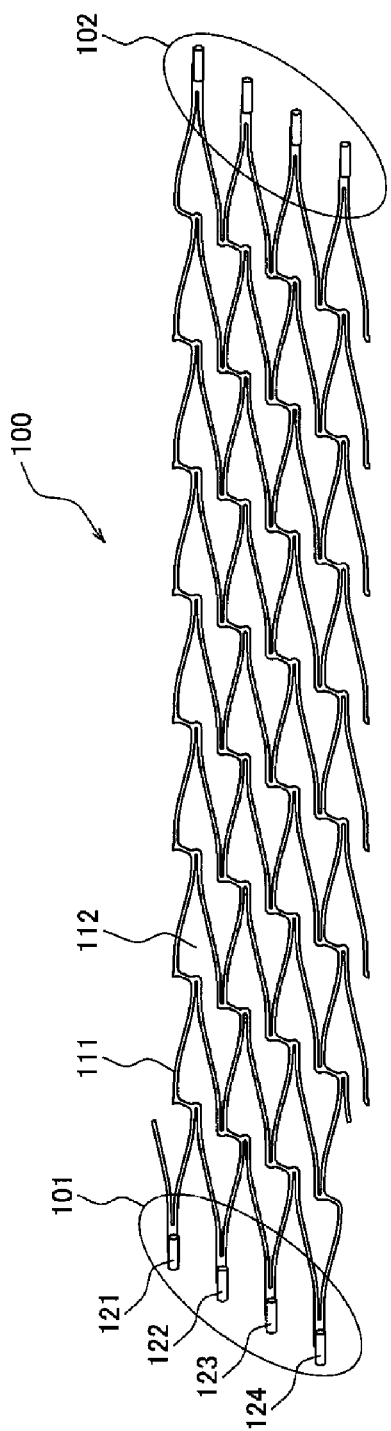
FIG. 8 shows a developed view of a medical tubular body according to a fourth embodiment of the present invention.

Hereinafter, a medical tubular body according to a fourth embodiment of the present invention is explained, referring to the drawings. FIG. 8 shows a developed view of a medical tubular body according to the fourth embodiment of the present invention. A medical tubular body 100 has a distal end 101 and a proximal end 102, and comprises a metal mesh 111 provided between the distal end 101 and the proximal end 102. The metal mesh 111 is configured by a combination of a sequence of cells 112 aligned in a helical direction. The medical tubular body 100 according to the fourth embodiment of the present invention basically has the similar constitution to the medical tubular body 100 according to the third embodiment of the present invention, and therefore, the same element is assigned with the same reference numeral, thereby omitting the explanation of it.

The medical tubular body 100 according to the fourth embodiment of the present invention is different from the medical tubular body 100 according to the third embodiment in that: in the third embodiment, the lengths of the support rods 151 to 154 are made to be different from each other, thereby providing the markers 121 to 124 at different positions from each other in the axial direction of the tubular body, whereas in the fourth embodiment, the metal mesh 111 is configured by a sequence of cells 112 aligned in the helical direction, thereby providing the markers 121 to 124 at different positions from each other in the axial direction of the tubular body, as shown in FIG. 8.

Figure 10:
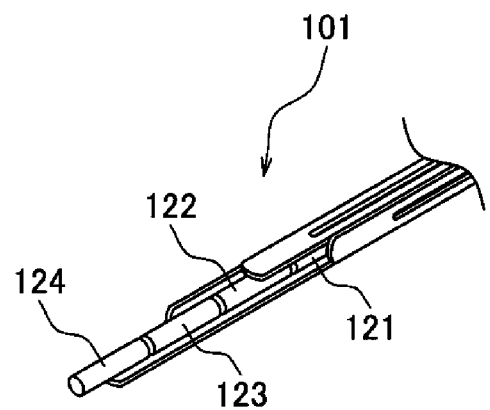
FIG. 10(a) shows a perspective view of the end part of the medical tubular body (in the diameter reduction state) according to the fourth embodiment.
FIG. 10(b) shows a view of the medical tubular body (in the diameter reduction state) according to the fourth embodiment seen from the axial direction.
Figure 10:
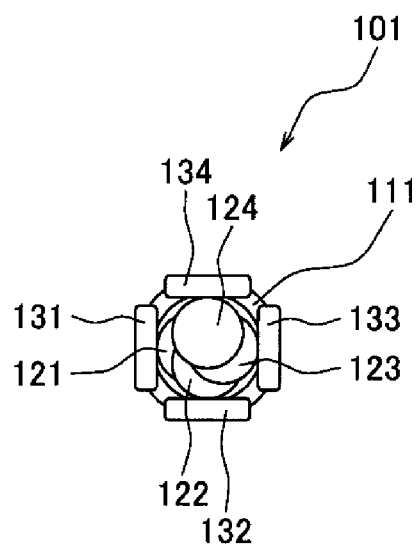

FIG. 9(a) shows a perspective view around the distal end 101 of the medical tubular body (in the diameter enlargement state) according to the fourth embodiment, and FIG. 9(b) shows a view of the distal end 101 thereof seen from the axial direction. FIG. 10(a) shows a perspective view around the distal end 101 of the medical tubular body (in the diameter reduction state) according to the fourth embodiment, and FIG. 9(b) shows a view of the distal end 101 thereof seen from the axial direction.

As can be seen from FIGS. 10(a), (b), since the markers 121 to 124 are provided at different positions from each other in the axial direction of the tubular body, the markers 121 to 124 can be placed in the inner space of the tubular body without interfering with each other when the tubular body is reduced in diameter. In the case that the medical tubular body 100 comprises two or more of the markers like this, it can be seen that providing the respective markers at different positions in the axial direction of the tubular body is effective technique to decrease the diameter of the medical tubular body 100 in the reduced state. In the third embodiment, the support rod is likely to be distorted in a biological lumen in the case where the support rod is formed so long; however, according to the present embodiment, since the end part of the tubular body is formed obliquely by the configuration of the metal mesh 111 itself, it is advantageous that there is no need to use the long support rod and the rigidity of the end part of the tubular body can be maintained.

In the fourth embodiment, the markers 121 to 124 are aligned in a straight line at a certain angle to the axial direction of the medical tubular body 100, as can be seen from FIG. 8. FIG. 8 shows a developed view, and when the medical tubular body 100 formed into a tubular shape by rolling the metal mesh 111 is observed from the side, the markers 121 to 124 are seen to be aligned in a straight line. This is because the end part of the tubular body forms a cylindrical shape cut diagonally (i.e., a shape like a tip of a syringe needle). As the diameter of the tubular body is gradually reduced, the angle between the straight line in which the markers 121 to 124 are aligned and the axial direction of the tubular body becomes smaller. And the reduction of the tubular body is completed, the straight line in which the markers 121 to 124 are aligned becomes parallel to the axis of the tubular body. By utilizing this movement of the markers, the degree of expansion and contraction of the tubular body, that is, for example, a diameter enlargement state, a diameter semi-enlargement state or a diameter reduction state, can be estimated from the angle between the straight line in which the markers 121 to 124 are aligned and the axis of the tubular body.

As shown in FIG. 10(b) a little extremely, some clearance may be formed adjacent to the markers 121 to 124 on the opposite side of the side fixed to the marker housings 131 to 134, and the makers 121 to 124 may not be completely lied on a straight line in the axial direction of the tubular body in the diameter reduction state. Of course, that the markers 121 to 124 are completely lied on the straight line is ideal in respect that the markers having a large volume can be placed by utilizing the inner space of the tubular body at a maximum; however, since the tubular body is not always reduced in diameter as designed, remaining some clearance may advantageously serve to the reduction of the diameter of the tubular body. Accordingly, it is one preferred embodiment to employ the constitution that the markers 121 to 124 are not lied on the straight line in the state where the tubular body is reduced in diameter.

(Embodiment 5)

Figure 11:
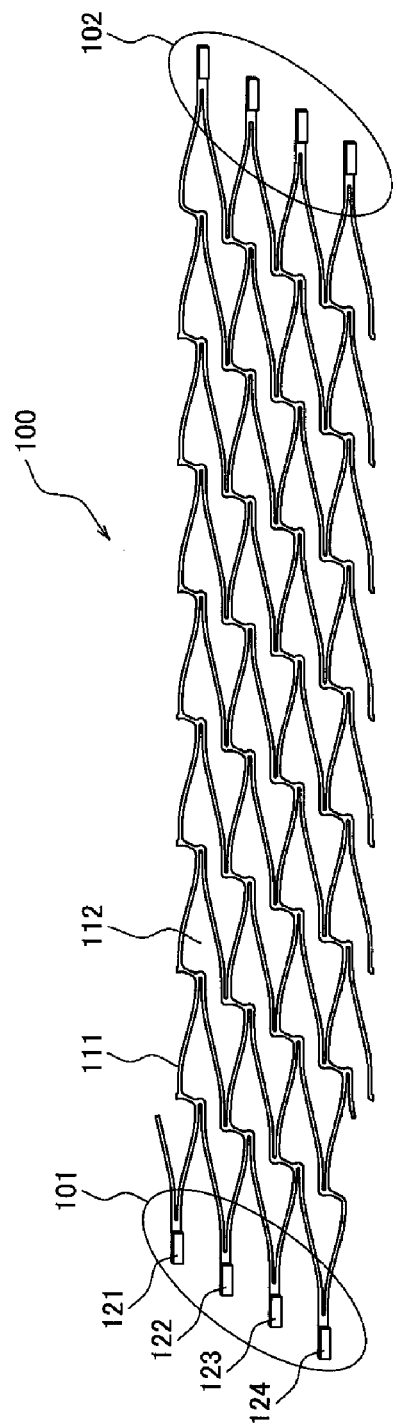
FIG. 11 shows a developed view of a medical tubular body according to a fifth embodiment of the present invention.
Figure 13:
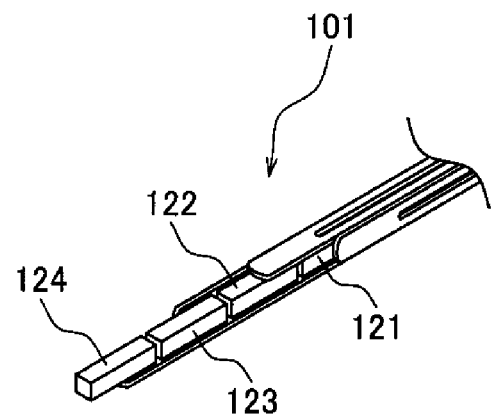
FIG. 13(a) shows a perspective view of the end part of the medical tubular body (in the diameter reduction state) according to the fifth embodiment.
FIG. 13(b) shows a view of the medical tubular body (in the diameter reduction state) according to the fifth embodiment seen from the axial direction.
Figure 13:
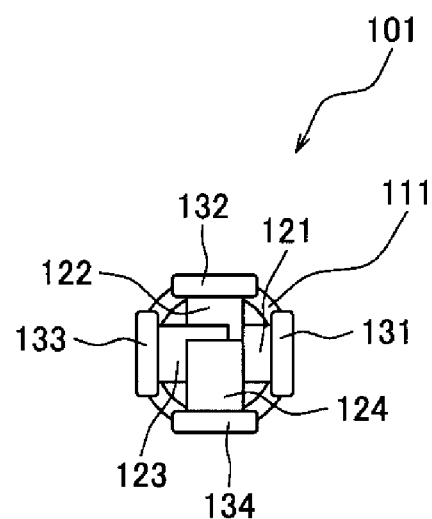

Hereinafter, a medical tubular body according to a fifth embodiment of the present invention is explained, referring to the drawings. FIG. 11 shows a developed view of a medical tubular body according to the fifth embodiment of the present invention. FIG. 12(a) shows a perspective view around the distal end 101 of the medical tubular body (in the diameter enlargement state) according to the fifth embodiment, and FIG. 12(b) shows a view of the distal end 101 thereof seen from the axial direction. Further, FIG. 13(a) shows a perspective view around the distal end 101 of the medical tubular body (in the diameter reduction state) according to the fifth embodiment, and FIG. 13(b) shows a view of the distal end 101 thereof seen from the axial direction.

The medical tubular body 100 according to the fifth embodiment of the present invention has the almost similar constitution to the medical tubular body 100 according to the fourth embodiment of the present invention; however, they are different from each other in that: in the fourth embodiment, the markers 121 to 124 are formed to be a circular columnar shape, whereas in the fifth embodiment, the markers 121 to 124 are formed to be a prismatic columnar shape. When the markers 121 to 124 have a prismatic columnar shape, the contact surfaces with the marker housings 131 to 134 are enlarged, that is advantageous in terms of the anchorage strength.

The medical tubular bodies according to the embodiments of the present invention are explained above with reference to specific examples; however, the present invention is not restricted by the above embodiments and can be put into practice after appropriate modifications within a range meeting the gist of the above and the below, all of which are included in the technical scope of the present invention.

The medical tubular body represented by a stent contracts in the radial direction in a cross-section perpendicular to the longitudinal axis of the tubular body and extends in the longitudinal axis direction in the diameter reduction state of being placed in a catheter, and forms a cylindrical shape which is longer and shorter than in the diameter enlargement state. Due to the structure of a catheter, in the medical tubular body of the self-expandable type, the outer diameter in the reduced state needs to be made smaller than that of the balloon expanding type. Therefore, the medical tubular body of the present invention, that is able to make the outer diameter in the reduced state small, is more preferably applied to the self-expandable type.

In addition to the above instance, the medical tubular body of the present invention can be applied to various medical tubular bodies such as a drug-coated stent, a biodegradable stent and the like.

REFERENCE SIGNS LIST

100: a medical tubular body
101: a distal end
102: a proximal end
111: a metal mesh
112: a cell
121, 122, 123, 124: a marker
131, 132, 133, 134: a marker housing
141: an inner surface of the marker housing
151, 152, 153, 154: a support rod

The invention claimed is:

1. A medical tubular body comprising a tubular body whose diameter is expandable and at least two markers containing an X-ray opaque material, provided inside the tubular body and not provided outside the tubular body, wherein
said at least two markers are provided at different positions in a circumferential direction of the tubular body, and
parts of said at least two markers are overlapped with each other when viewed from a longitudinal axis direction of the tubular body in the state where the tubular body is reduced in diameter.

2. The medical tubular body according to claim 1, wherein at least one of said at least two markers is provided at a non-deformation part which constitutes a part of the tubular body.

3. The medical tubular body according to claim 1, wherein at least one of said at least two markers is provided at a plane part of the inner surface of the tubular body.

4. The medical tubular body according to claim 1, wherein at least one of said at least two markers is welded to the inner surface of the tubular body.

5. The medical tubular body according to claim 1, wherein at least one of said at least two markers has a size so as to be placed in an inner space of the tubular body in a state where the tubular body is reduced in diameter.

6. The medical tubular body according to claim 1,
wherein said at least two markers have a size so as not to contact with each other in the state where the tubular body is reduced in diameter.

7. The medical tubular body according to claim 1, further comprising a plurality of support rods whose lengths are different from each other,
wherein at least one of said at least two markers is provided at an end part of each of the support rods.

8. The medical tubular body according to claim 1, wherein clearance is formed between one end of at least one of said at least two markers and the tubular body in the state where the tubular body is reduced in diameter.

9. The medical tubular body according to claim 1, wherein at least one of said at least two markers is longer in the longitudinal axis direction of the tubular body than in a radial direction of the tubular body.

10. The medical tubular body according to claim 1, wherein the medical tubular body is self-expandable.

11. The medical tubular body according to claim 1, wherein the tubular body has a net-shaped structure configured by a combination of a sequence of cells aligned in a helical direction.

12. The medical tubular body according to claim 1, wherein said at least two markers are provided at different positions in the longitudinal axis direction of the tubular body.

13. The medical tubular body according to claim 1, wherein the medical tubular body is a thrombus recovery device that removes a thrombus.

14. The medical tubular body according to claim 1, wherein said at least two markers extend only inwardly from an inner surface of the tubular body.

15. The medical tubular body according to claim 1, wherein said at least two markers extend only radially inward from an inner surface of the tubular body.

16. The medical tubular body according to claim 1, wherein said at least two markers extend inwardly from an inner surface of the tubular body, but not outwardly from the inner surface of the tubular body in a radial direction of the tubular body.

* * * * *